US012734371B2

(12) United States Patent
Kim

(10) Patent No.: US 12,734,371 B2
(45) **Date of Patent: *Sep. 15, 2026**

(54) MAGNETIC STIMULATION APPARATUS

(71) Applicant: Remed Co., Ltd, Daejeon (KR)

(72) Inventor: Ghi Young Kim, Gyeonggi-Do (KR)

(73) Assignee: Remed Co., Ltd, Daejeon (KR)

( * ) Notice: Subject to any disclaimer, the term of this patent is extended or adjusted under 35 U.S.C. 154(b) by 722 days.

This patent is subject to a terminal disclaimer.

(21) Appl. No.: 18/032,897

(22) PCT Filed: Oct. 5, 2021

(86) PCT No.: PCT/KR2021/013569

§ 371 (c)(1),
(2) Date: Apr. 20, 2023

(87) PCT Pub. No.: WO2022/085989

PCT Pub. Date: Apr. 28, 2022

(65) Prior Publication Data

US 2023/0381530 A1 Nov. 30, 2023

(30) Foreign Application Priority Data

Oct. 23, 2020 (KR) ........................ 10-2020-0138448

(51) Int. Cl.
*A61N 2/02* (2006.01)
*A61N 2/00* (2006.01)
*H05K 7/20* (2006.01)

(52) U.S. Cl.
CPC ............... *A61N 2/02* (2013.01); *A61N 2/004* (2013.01); *H05K 7/20272* (2013.01)

(58) Field of Classification Search
CPC ...... A61N 2/02; A61N 2/004; H01F 27/2876; H01F 27/10; F16B 37/122
(Continued)

(56) References Cited

U.S. PATENT DOCUMENTS 4,140,040 A 2/1979 Modrey
2002/0103411 A1 8/2002 Bailey et al.
(Continued)

FOREIGN PATENT DOCUMENTS

CN 109276812 A 1/2019
CN 110124200 A 8/2019
(Continued)

OTHER PUBLICATIONS

ISA/EPO International Search Report and Written Opinion for corresponding International Application No. PCT/KR2021/013569 dated Aug. 1, 2024 (7 pages).
(Continued)

*Primary Examiner* — Kaylee R Wilson
(74) *Attorney, Agent, or Firm* — Harris Beach Murtha Cullina PLLC

(57) ABSTRACT

Disclosed is a magnetic field stimulation device according to several embodiments of the present disclosure. The magnetic field stimulation device may include housings, inner casings having an internal space and accommodated in an accommodation space provided in the housings, a magnetic field generating means disposed in the internal space and configured to generate a magnetic field, and a cooling medium stored in the internal space and configured to induce the cooling of the magnetic field generating means.

11 Claims, 4 Drawing Sheets

(58) Field of Classification Search
USPC ........................................................ 600/13
See application file for complete search history.

(56) References Cited

U.S. PATENT DOCUMENTS

| | | | | |
|---|---|---|---|---|
| 2009/0108969 | A1 | 4/2009 | Sims et al. | |
| 2012/0245403 | A1* | 9/2012 | Martinez | A61N 1/40 600/13 |
| 2014/0165369 | A1* | 6/2014 | Chan | F16B 37/122 411/366.1 |

FOREIGN PATENT DOCUMENTS

| | | | |
|---|---|---|---|
| JP | 2012125546 | A | 7/2012 |
| KR | 20030065126 | A | 8/2003 |
| KR | 2008-0063077 | A | 7/2008 |
| KR | 10-1216494 | B1 | 12/2012 |
| KR | 101673182 | B1 | 11/2016 |
| KR | 20180059114 | A | 6/2018 |
| KR | 102046924 | B1 | 11/2019 |
| KR | 2020-0110632 | A | 9/2020 |

OTHER PUBLICATIONS

ISA/KR International Search Report and Written Opinion for corresponding International Application No. PCT/FR2021/013569 dated Jan. 10, 2022 (3 pages).

* cited by examiner

MAGNETIC STIMULATION APPARATUS

CROSS-REFERENCE TO RELATED APPLICATIONS

This application is a national stage application under 35 U.S.C. § 371 of PCT Application No. PCT/KR2021/013569, filed on Oct. 5, 2021, which claims priority to and the benefit of Korean Patent Application No. 10-2020-0138448 filed on Oct. 5, 2021.

TECHNICAL FIELD

The present disclosure relates to a magnetic field stimulation device, and more particularly, to a device that stimulates a patient's skin by using a magnetic field.

BACKGROUND ART

Recently, there have been known technologies related to a magnetic field stimulation device that promotes treatment for the purpose of skin care and cure by using a magnetic field generated by the magnetic field stimulation device.

In general, the magnetic field stimulation device may have a magnetic field generating means such as a coil provided therein and generate a magnetic field. In this case, a temperature of the magnetic field generating means may be raised to 70° C. or more to generate the magnetic field. Therefore, the magnetic field stimulation device generally sometimes has a cooling medium such as cooling oil provided therein, and the cooling medium cools the magnetic field generating means. In this case, the magnetic field generating means may also generate vibration with 30 Hz or higher per second while consistently dissipating heat with a temperature of 70° C. or more. In this case, a crack or the like may be formed in a housing that forms an external shape of the magnetic field stimulation device. Furthermore, a crack may be formed in the housing by various external factors. However, in case that the crack is formed in the housing, the cooling medium such as cooling oil leaks, which may cause fatal damage to a patient.

Therefore, there is a need to develop a magnetic field stimulation device that is safe even in a case in which a crack is formed in the housing.

SUMMARY OF THE INVENTION

The present disclosure has been made in an effort to provide a magnetic field stimulation device that is safe even in a case in which a crack is formed in a housing.

Technical problems of the present disclosure are not limited to the aforementioned technical problems, and other technical problems, which are not mentioned above, may be clearly understood by those skilled in the art from the following descriptions.

In order to achieve the above-mentioned object, an exemplary embodiment of the present disclosure provides a magnetic field stimulation device. The magnetic field stimulation device may include housings, inner casings having an internal space and accommodated in an accommodation space provided in the housings, a magnetic field generating means disposed in the internal space and configured to generate a magnetic field, and a cooling medium stored in the internal space and configured to induce the cooling of the magnetic field generating means.

The inner casings may include a first casing and a second casing that form the internal space, the first casing may include a first coupling portion protruding from an outer peripheral surface of the first casing along a periphery of the first casing and having a first fastening hole, and the second casing may include a second coupling portion protruding from an outer peripheral surface of the second casing along a periphery of the second casing and having a second fastening hole provided at a position corresponding to the first fastening hole.

The housings may include a first housing and a second housing that form the accommodation space, and the first housing may have a fastening groove provided at a position corresponding to the first fastening hole and the second fastening hole.

The first housing, the first casing, and the second casing may be coupled to one another as the first fastening hole, the second fastening hole, and the fastening groove are fastened by a fastening means.

The magnetic field stimulation device may further include: an insert member fixedly coupled in the fastening groove and having an internal thread.

The second housing may have a protruding portion provided on a junction surface of the second housing to which the first housing is joined, the protruding portion may extend and protrude along the junction surface, and the first housing may have a coupling groove provided at a position corresponding to the protruding portion.

The first housing and the second housing may be coupled to each other as the protruding portion and the coupling groove are fitted with each other.

The magnetic field stimulation device may further include: a first sealing member provided between the first casing and the second casing and configured to prevent the cooling medium from leaking outside.

The first casing may have a first hole through which the cooling medium enters or exits the first casing, the first housing may have a first passageway through which the cooling medium enters or exits the first housing, the first passageway may be provided at a position corresponding to the first hole, and the second casing may have a second passageway through which the cooling medium enters or exits the second casing.

The magnetic field stimulation device may further include: a second sealing member provided between the first housing and the second housing and configured to prevent the cooling medium from leaking outside.

The first casing may include a seating portion having a shape corresponding to the magnetic field generating means so that the magnetic field generating means is seated on the seating portion.

The first casing may be coupled to the first housing so as to be in close contact with an inner surface of the first housing in which the accommodation space is formed.

The technical solutions obtained by the present disclosure are not limited to the aforementioned technical solutions, and other technical solutions, which are not mentioned above, will be clearly understood by those skilled in the art from the following description.

According to the several embodiments of the present disclosure, it is possible to provide the safe magnetic field stimulation device.

The effects obtained by the present disclosure are not limited to the aforementioned effects, and other effects, which are not mentioned above, will be clearly understood by those skilled in the art from the following description.

BRIEF DESCRIPTION OF THE DRAWINGS

Various aspects will be described with reference to the drawings, in which similar reference numerals are used to refer to similar components. In the following examples, for purposes of explanation, multiple specific details are set forth in order to provide a thorough understanding of one or more aspects. However, it will be apparent that such aspect(s) may be practiced without the specific details. In other examples, publicly known structures and devices are illustrated in block diagrams in order to easily describe one or more aspects.

DETAILED DESCRIPTION

Figure 1:
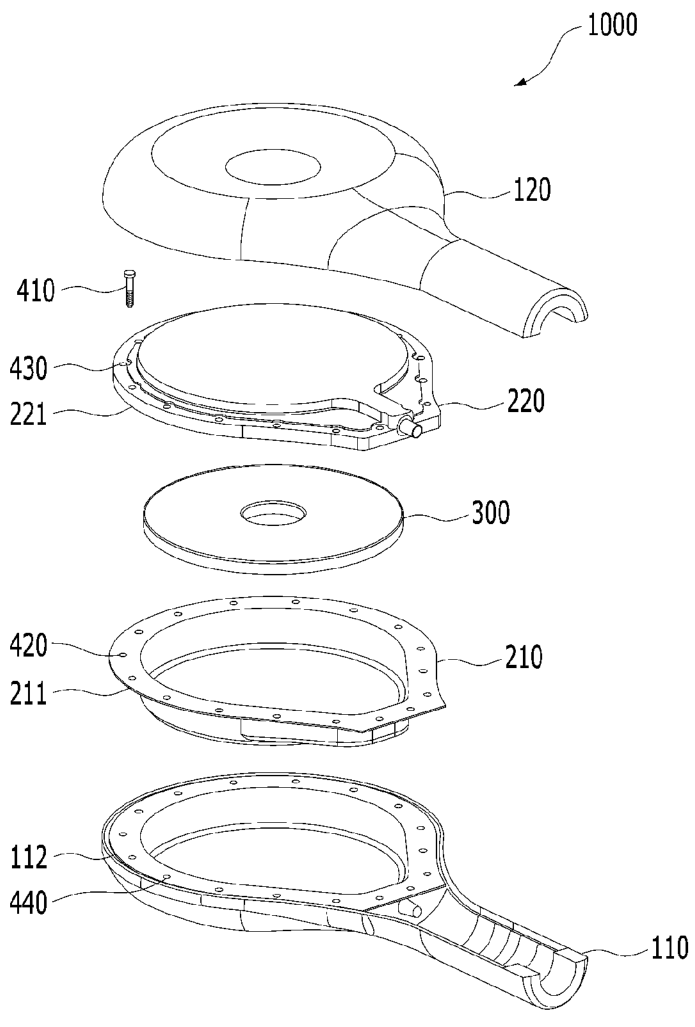
FIG. 1 is an exploded perspective view for explaining an example of a magnetic field stimulation device according to several embodiments of the present disclosure.

Various embodiments and/or various aspects will be disclosed with reference to the drawings. In the following descriptions, for explanation, multiple specific details are disclosed in order to provide overall understandings of one or more aspects. However, it will also be appreciated by those skilled in the art that this aspect(s) may be practiced without these specific details. The following descriptions and the accompanying drawings are provided for disclosing specific exemplary aspects of the one or more aspects in detail. However, these aspects are exemplary. Thus, some of the various methods in the principles of the various aspects may be used, and the descriptions are intended to include all such aspects and their equivalents. Specifically, "embodiment", "example", "aspect", "exemplary embodiment" and the like used in this specification may not be construed as any aspect or design described being better or more advantageous than other aspects or designs.

Hereinafter, the same or similar constituent elements are assigned with the same reference numerals regardless of reference numerals, and the repetitive description thereof will be omitted. In addition, in the description of the embodiment disclosed in the present specification, the specific descriptions of publicly known related technologies will be omitted when it is determined that the specific descriptions may obscure the subject matter of the embodiment disclosed in the present specification. In addition, the accompanying drawings are provided only to allow those skilled in the art to easily understand the embodiments disclosed in the present specification, and the technical spirit disclosed in the present specification is not limited by the accompanying drawings.

Terms "first", "second", and the like may be used to describe various elements and components, but the elements and components are of course not limited by these terms. These terms are merely used to distinguish one element or component from another element or component. Therefore, the first element or component mentioned hereinafter may of course be the second element or component within the technical spirit of the present disclosure.

Unless otherwise defined, all terms (including technical and scientific terms) used in the present specification may be used as the meaning which may be commonly understood by the person with ordinary skill in the art, to which the present disclosure belongs. In addition, terms defined in a generally used dictionary shall not be construed in ideal or excessively formal meanings unless they are clearly and specially defined in the present specification.

The term "or" is intended to mean not an exclusive "or" but an inclusive "or". That is, unless specified or clear in context, "X uses A or B" is intended to mean one of the natural implicit substitutions. That is, "X uses A or B" can be applied to any of the cases where X uses A, X uses B, or X uses both A and B. Moreover, it is to be understood that the term "and/or" used in this specification refers to and includes all possible combinations of one or more of the listed related items.

It is to be understood that the terms "comprise (include)" and/or "comprising (including)" mean that the feature and/or a component is provided, but the presence or addition of one or more other features, other components and/or groups thereof are not excluded. In addition, unless specified or clear in the context of indicating a singular form, the singular in this specification and claims should generally be construed to mean "one or more".

When one constituent element is described as being "connected" or "coupled" to another constituent element, it should be understood that one constituent element can be connected or coupled directly to another constituent element, and an intervening constituent element can also be present between the constituent elements. When one constituent element is described as being "connected directly to" or "coupled directly to" another constituent element, it should be understood that no intervening constituent element is present between the constituent elements.

The suffixes "module" and "unit" used to describe some constituent elements in the following description are used together or interchangeably in order to facilitate the description, but the suffixes themselves do not have distinguishable meanings or functions.

When an element or layer is referred to as being "on" another element or layer, it can be directly on the other element or layer or intervening elements or layers may be present. In contrast, when an element is referred to as being "directly on" another element or layer, there are no intervening elements or layers present.

Spatially relative terms, such as "below," "beneath," "lower," "above," "upper," and the like, may be used herein for ease of description of one constituent element or a correlation between one constituent element and other constituent elements, as illustrated in the drawings. It should be understood that the spatially relative terms encompass different orientations of the elements in use or operation in addition to the orientation depicted in the drawings.

For example, if the constituent element in the drawings is turned over, the constituent element described as "below" or "beneath" the other constituent element may then be placed "above" the other constituent element. Thus, the exemplary term "below" can encompass both orientations of above and below. The constituent elements may be oriented in different directions, and the spatially relative terms used herein may be interpreted in accordance with the orientations.

Objects and effects of the present disclosure and technical constituent elements for achieving the objects and effects will be clear with reference to the embodiments described in detail below together with the accompanying drawings. In addition, in the description of the present disclosure, the specific descriptions of publicly known functions or configurations will be omitted when it is determined that the specific descriptions may unnecessarily obscure the subject matter of the present disclosure. In addition, the terms used herein are defined considering the functions in the present disclosure and may vary depending on the intention or usual practice of a user or an operator.

However, the present disclosure is not limited to the embodiments disclosed herein but will be implemented in various forms. The embodiments of the present disclosure are provided so that the present disclosure is completely disclosed, and a person with ordinary skill in the art can fully understand the scope of the present disclosure. The present disclosure will be defined only by the scope of the appended claims. Therefore, the definition of the present disclosure should be made based on the entire contents of the present specification.

In the present disclosure, a magnetic field stimulation device may promote treatment for the purpose of skin care and cure by using a magnetic field. For example, the magnetic field stimulation device may generate the magnetic field by using a magnetic field generating means provided in a housing that forms an external shape of the magnetic field stimulation device. In this case, the magnetic field generating means may generate a high temperature and vibration while generating the magnetic field. In this case, a crack or the like may be formed in the housing by the high temperature and vibration. Therefore, in the present disclosure, an inner casing may be further provided to prevent a cooling medium provided in a magnetic field generating device from leaking even though a crack is formed in the housing. Hereinafter, the magnetic field stimulation device according to the present disclosure will be described with reference to FIGS. 1 to 4.

FIG. 1 is an exploded perspective view for explaining an example of the magnetic field stimulation device according to several embodiments of the present disclosure.

With reference to FIG. 1, a magnetic field stimulation device 1000 may include housings 110 and 120, inner casings 210 and 220, and a magnetic field generating means 300. However, the above-mentioned constituent elements are not essential to implement the magnetic field stimulation device 1000. The magnetic field stimulation device 1000 may have the constituent elements larger or smaller in number than the constituent elements listed above.

The housings 110 and 120 may form an external shape of the magnetic field stimulation device 1000.

The housings 110 and 120 may have a shape corresponding to the magnetic field generating means 300 so that the magnetic field generating means 300 may be provided in the housings 110 and 120. However, the present disclosure is not limited thereto.

Meanwhile, the housings 110 and 120 may each have a handle that allows a user to conveniently grip the magnetic field stimulation device 1000. However, the present disclosure is not limited thereto.

Meanwhile, the housings 110 and 120 may include a first housing 110 and a second housing 120. Further, the housings 110 and 120 may form an accommodation space as the first housing 110 and the second housing 120 are coupled to each other, and the internal constituent elements may be accommodated in the accommodation space. However, the present disclosure is not limited thereto.

Meanwhile, according to the several embodiments of the present disclosure, a protruding portion (not illustrated) may be provided on a junction surface of the second housing 120 to which the first housing 110 is joined, and the protruding portion may extend and protrude along the junction surface. Further, the first housing 110 may have a coupling groove 112 provided at a position corresponding to the protruding portion. In this case, the first housing 110 and the second housing 120 may be coupled to each other as the protruding portion and the coupling groove are fitted with each other. However, the present disclosure is not limited thereto. Hereinafter, the protruding portion and the coupling groove 112 according to the present disclosure will be described below with reference to FIG. 3.

Meanwhile, the inner casings 210 and 220 may be accommodated in the accommodation space provided in the housings 110 and 120 and have an internal space.

For example, the inner casings 210 and 220 may include a first casing 210 and a second casing 220 that form the internal space in which the magnetic field generating means 300 may be provided. However, the present disclosure is not limited thereto.

Meanwhile, according to the several embodiments of the present disclosure, the first casing 210 may include a first coupling portion 211 protruding from an outer peripheral surface of the first casing 210 along a periphery of the first casing 210 and having a first fastening hole 420. In this case, the first fastening hole 420 may be provided as a plurality of first fastening holes 420. In addition, the second casing 220 may include a second coupling portion 221 protruding from an outer peripheral surface of the second casing 220 along a periphery of the second casing 220 and having a second fastening hole 430 provided at a position corresponding to the first fastening hole 420. In this case, the second fastening hole 430 may be provided as a plurality of second fastening holes 430 corresponding in number to the first fastening holes 420. However, the present disclosure is not limited thereto.

Meanwhile, the first casing 210 and the second casing 220 may be fastened by fastening means 410 corresponding in number to the first fastening holes 420 and the second fastening holes 430. For example, the fastening means 410 may be a bolt or the like. However, the present disclosure is not limited thereto. The fastening means 410 may penetrate the first fastening hole 420 and the second fastening hole 430 and be fastened to the first housing 110.

Meanwhile, the first casing 210 and the second casing 220 may be coupled to the first housing 110 by means of the fastening means 410.

Specifically, the first housing 110 may have fastening grooves 440 provided at positions corresponding to the first fastening holes 420 and the second fastening holes 430. In this case, the fastening grooves 440 may correspond in number to the plurality of first fastening holes 420 and the plurality of second fastening holes 430. In this case, the first housing 110, the first casing 210, and the second casing 220 may be coupled to one another by means of the fastening means 410 fastened to the first fastening hole 420, the second fastening hole 430, and the fastening groove 440. However, the present disclosure is not limited thereto.

Meanwhile, according to the several embodiments of the present disclosure, the magnetic field stimulation device 1000 may further include an insert member (not illustrated) fixedly coupled in the fastening groove 440 and having an internal thread. In this case, the fastening groove 440 provided in the first housing 110 is not fastened directly to the fastening means 410, which makes it possible to prevent a crack or the like from being formed in the fastening groove 440 by the fastening means 410. Further, in case that a crack or the like is formed in the fastening groove 440, a crack may also be formed in the first housing 110. Therefore, the insert member may be provided in the present disclosure. However, the present disclosure is not limited thereto. Hereinafter, the insert member according to the present disclosure will be described below with reference to FIG. 3.

Meanwhile, in the present disclosure, it is difficult to use a metallic material for the inner casings 210 and 220 because of induction heating made by a magnetic field generated by the magnetic field generating means 300. Therefore, the inner casings 210 and 220 may each be made of at least one material among synthetic resin, synthetic rubber, and PET. However, the present disclosure is not limited thereto. In addition, the housings 110 and 120 may also be made of at least one material among synthetic resin, synthetic rubber, and PET. However, the housings 110 and 120 may each be made of a metallic material.

Meanwhile, in the present disclosure, the first casing 210 may be manufactured by vacuum forming or pressure forming. However, the present disclosure is not limited thereto.

Meanwhile, the magnetic field generating means 300 may be disposed in the internal space formed by the first casing 210 and the second casing 220 and generate the magnetic field.

For example, the magnetic field generating means 300 may be a coil or the like. However, the present disclosure is not limited thereto.

Meanwhile, according to the several embodiments of the present disclosure, the first casing 210 may have a seating portion (not illustrated) having a shape corresponding to the magnetic field generating means 300 so that the magnetic field generating means 300 is seated on the seating portion. In this case, the magnetic field generating means 300 may be seated on the seating portion without moving in the internal space even though vibration is generated when the magnetic field is generated. Hereinafter, the seating portion will be described below with reference to FIG. 4.

Meanwhile, the magnetic field stimulation device 1000 may include a cooling medium (not illustrated) for cooling the magnetic field generating means.

Specifically, the cooling medium may be stored in the internal space formed by the first casing 210 and the second casing 220 and cool the magnetic field generating means 300. In this case, the cooling medium may be cooling oil or the like. However, the present disclosure is not limited thereto.

Meanwhile, according to the several embodiments of the present disclosure, the magnetic field stimulation device 1000 may further include a first sealing member (not illustrated) provided between the first casing 210 and the second casing 220 and configured to prevent the cooling medium from leaking outside. In this case, a sealing member groove (not illustrated) may be provided in the second casing 220, and the first sealing member may be inserted into the sealing member groove. Hereinafter, the sealing member groove provided in the second casing 220 according to the present disclosure will be described below with reference to FIG. 3.

Meanwhile, according to the several embodiments of the present disclosure, the magnetic field stimulation device 1000 may further include a second sealing member provided between the first housing and the second housing and configured to prevent the cooling medium from leaking outside. However, the present disclosure is not limited thereto.

With the above-mentioned configuration, the magnetic field stimulation device 1000 may have the housings 110 and 120 and the inner casings 210 and 220. Further, the magnetic field generating means 300 and the cooling medium may be provided in the internal space provided in the inner casings 210 and 220. In this case, the inner casings 210 and 220 may prevent the cooling medium from leaking outside even though a crack or the like is formed in the housings 110 and 120 because of eventuality. Therefore, the user's safety may be ensured.

Figure 2:
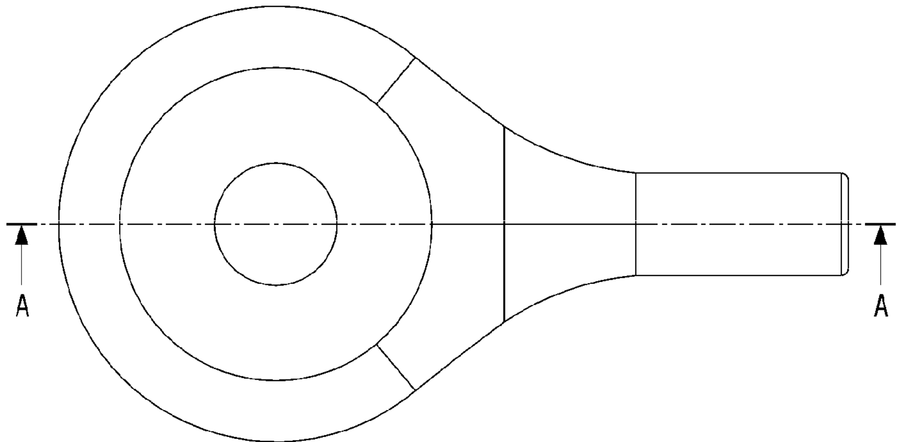
FIG. 2 is a top plan view for explaining an example of the magnetic field stimulation device according to the several embodiments of the present disclosure.
Figure 3:
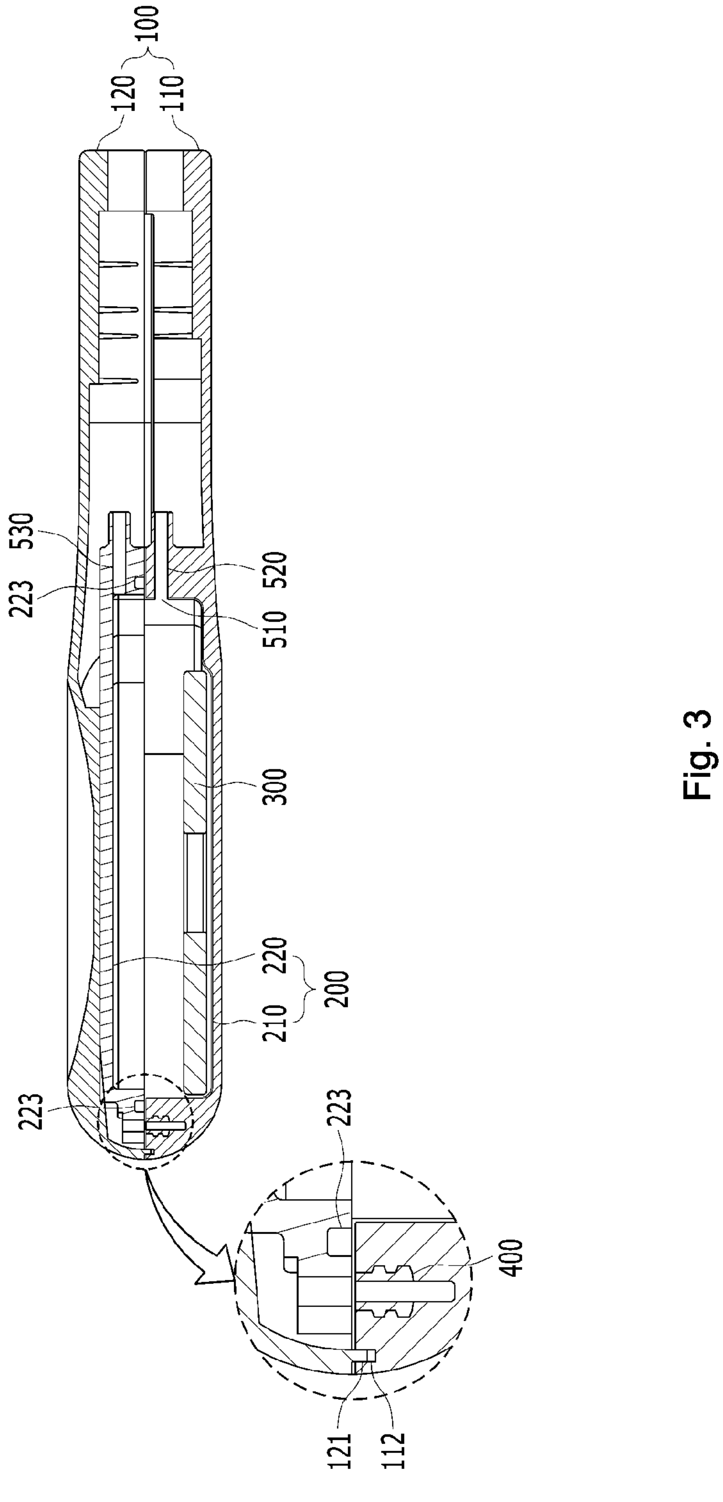
FIG. 3 is a cross-sectional view taken along line A-A' in FIG. 2 for explaining an example of the magnetic field stimulation device according to the several embodiments of the present disclosure.

FIG. 2 is a top plan view for explaining an example of the magnetic field stimulation device according to the several embodiments of the present disclosure. FIG. 3 is a cross-sectional view taken along line A-A' in FIG. 2 for explaining an example of the magnetic field stimulation device according to the several embodiments of the present disclosure.

With reference to FIG. 3, the magnetic field stimulation device 1000 may include a housing 100 and an inner casing 200.

In this case, the cooling medium may be introduced from the outside or discharged to the outside through a passageway provided in the magnetic field stimulation device 1000. For example, the magnetic field stimulation device 1000 may be connected to an external tank in which the cooling medium is stored. Further, the cooling medium stored in the internal space of the inner casing 200 may be replaced with the cooling medium stored in the external tank. To this end, the housing 100 and the inner casing 200 may respectively have holes or passageways through which the cooling medium enters or exits the housing 100 and the inner casing 200. In this case, it is possible to prevent a temperature of the cooling medium from being raised to an excessively high temperature by the magnetic field generating means 300.

Specifically, the first casing 210 may have a first hole 510 through which the cooling medium may enter or exit the first casing 210. Further, the first housing 110 may have a first passageway 520 through which the cooling medium may enter or exit the first housing 110, and the first passageway 520 may be provided at a position corresponding to the first hole 510. In this case, the cooling medium may be introduced into or discharged from the internal space of the inner casing 200 through the first hole 510 and the first passageway 520. However, the present disclosure is not limited thereto.

Meanwhile, the second casing 220 may have a second passageway 530 through which the cooling medium may enter or exit the second casing 220. Further, the cooling medium may be introduced into or discharged from the internal space of the inner casing 200 through the second passageway 530. However, the present disclosure is not limited thereto.

For example, the cooling medium may be introduced into the internal space through the first hole 510 and the first passageway 520 and discharged to the outside through the second passageway 530. As another example, the cooling medium may be discharged to the outside through the first hole 510 and the first passageway 520 and introduced into the internal space through the second passageway 530. Therefore, the cooling medium stored in the internal space may circulate. However, the present disclosure is not limited thereto.

Meanwhile, according to the several embodiments of the present disclosure, the first casing 210 may be coupled to the first housing 110 so as to be in close contact with an inner surface of the first housing 110 in which the accommodation space is formed. For example, the first casing 210 may be formed in a shape corresponding to the inner surface of the first housing 110. In this case, it is possible to prevent the cooling medium from being introduced between the first hole 510 provided in the first casing 210 and the first passageway 520 provided in the first housing 110. However, the present disclosure is not limited thereto.

Meanwhile, in the present disclosure, the first casing 210 and the first housing 110 may be coupled to each other by bonding. For example, a bonding agent may be applied onto a lower surface of the first casing 210 or the inner surface of the first housing 110 in which the accommodation space is formed. Further, the first casing 210 and the first housing 110 may be coupled to each other by the bonding agent. In this case, the first casing 210 may be coupled to the first housing 110 so as to be in close contact with the inner surface of the first housing 110. However, the present disclosure is not limited thereto.

Meanwhile, according to the several embodiments of the present disclosure, the sealing member may be provided between the first casing 210 and the first housing 110.

Specifically, the sealing member groove may be provided in the inner surface of the first housing 110 in which the accommodation space is provided, and the sealing member groove may be provided along a periphery of the first passageway 520. The sealing member may be inserted into the sealing member groove.

For example, the sealing member groove into which the sealing member, such as an O-ring, may be inserted may be provided in the inner surface. In this case, a diameter of the sealing member groove may be larger than a diameter of the first hole 510. In this case, it is possible to prevent the cooling medium from being introduced between the first hole 510 provided in the first casing 210 and the first passageway 520 provided in the first housing 110. However, the present disclosure is not limited thereto.

Meanwhile, according to the several embodiments of the present disclosure, a protruding portion 121 may be provided on the junction surface of the second housing 120 to which the first housing 110 is joined, and the protruding portion 121 may extend and protrude along the junction surface. Further, the first housing 110 may have the coupling groove 112 provided at a position corresponding to the protruding portion 121. In this case, the first housing 110 and the second housing 120 may be coupled to each other as the protruding portion 121 and the coupling groove 112 are fitted with each other. However, the present disclosure is not limited thereto.

Meanwhile, according to the several embodiments of the present disclosure, the protruding portion may be provided on the junction surface of the first housing 110 to which the second housing 120 is joined, and the protruding portion may extend and protrude along the junction surface. Further, the second housing 120 may have a coupling groove provided at a position corresponding to the protruding portion. However, the present disclosure is not limited thereto.

Meanwhile, according to the several embodiments of the present disclosure, the magnetic field stimulation device 1000 may further include the first sealing member (not illustrated) provided between the first casing 210 and the second casing 220 and configured to prevent the cooling medium from leaking outside. In this case, the second casing 220 may have a sealing member groove 223 into which the first sealing member is inserted. In this case, it is possible to prevent a leak of the cooling medium stored in the inner casing 200. However, the present disclosure is not limited thereto.

Meanwhile, according to the several embodiments of the present disclosure, the magnetic field stimulation device 1000 may further include an insert member 400 fixedly coupled in the fastening groove 440 and having an internal thread. For example, the insert member 400 may be inserted into the fastening groove 440 of the first housing 110. In this case, the fastening groove 440 provided in the first housing 110 is not fastened directly to the fastening means 410, which makes it possible to prevent the fastening groove 440 from being damaged by the fastening means 410. However, the present disclosure is not limited thereto.

Meanwhile, according to the several embodiments of the present disclosure, the first casing 210 may have the seating portion (not illustrated) having a shape corresponding to the magnetic field generating means 300 so that the magnetic field generating means 300 is seated on the seating portion. In addition, the inner surface of the first housing 110 in which the internal space is provided may have a shape corresponding to the seating portion. Hereinafter, a shape of the first casing 210 according to the present disclosure will be described with reference to FIG. 4.

Figure 4:
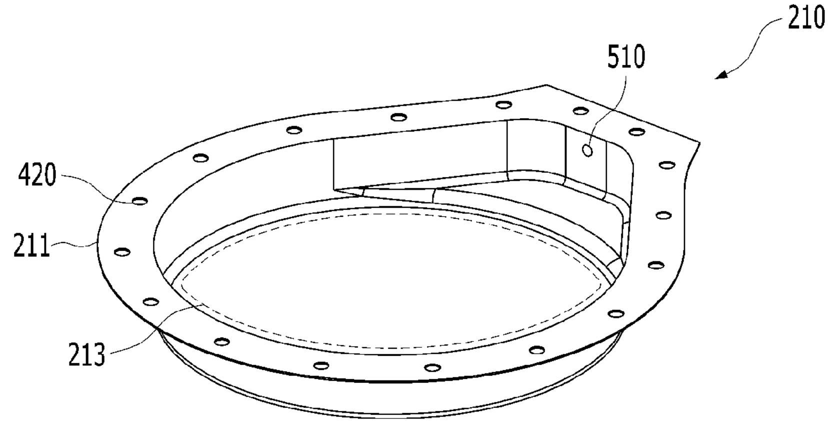
FIG. 4 is a perspective view for explaining an example of a first casing according to the several embodiments of the present disclosure.

FIG. 4 is a perspective view for explaining an example of the first casing according to the several embodiments of the present disclosure.

With reference to FIG. 4, the first casing 210 may have a seating portion 213, the first coupling portion 211, the first fastening hole 420, and the first hole 510. However, the present disclosure is not limited thereto.

The seating portion 213 may be formed in a shape corresponding to an external shape of the magnetic field generating means 300.

Specifically, the seating portion 213 may be formed in a shape corresponding to a shape of a lower portion of the magnetic field generating means 300. The seating portion 213 may be recessed in the inner surface of the first casing 210 in which the internal space is provided. In this case, the magnetic field generating means 300 may be seated on the seating portion 213. However, the present disclosure is not limited thereto.

Meanwhile, the first hole 510 of the first casing 210 may be provided at a position corresponding to the first passageway 520 of the first housing 110. That is, in case that the first casing 210 is coupled to the first housing 110, the cooling medium may be introduced from the outside or discharged to the outside through the first hole 510 and the first passageway 520. However, the present disclosure is not limited thereto.

As described above with reference to FIGS. 1 to 4, the magnetic field stimulation device 1000 may promote the treatment for the purpose of the user's skin care and cure by using the magnetic field generating means 300. In this case, a high temperature and vibration are generated when the magnetic field generating means 300 generates the magnetic field. The magnetic field stimulation device 1000 may be charged with the cooling medium to cool the magnetic field generating means 300. However, a temperature of the cooling medium is also raised to a temperature higher than the room temperature when the cooling medium cools the magnetic field generating means 300. For this reason, in case that the cooling medium leaks to the outside, the cooling medium may cause an injury to a patient. Therefore, in the present disclosure, the inner casing 200 may be provided in addition to the housing 100 to prevent the cooling medium from leaking patient. In this case, the cooling medium may be safely stored in the internal space of the inner casing 200 even though a crack or the like is formed in the housing 100 by an external factor or vibration generated by the magnetic field generating means 300.

The description of the provided embodiments is provided to enable any person skilled in the art of the present disclosure to carry out or use the present disclosure. Various modifications to the embodiments will be apparent to those skilled in the art of the present disclosure, and the generic principles defined herein may be applied to other embodiments without departing from the scope of the present disclosure. Accordingly, it should be understood that the present disclosure is not limited to the embodiments presented herein but should be construed in the broadest scope consistent with the principles and novel features presented herein.

What is claimed is:

1. A magnetic field stimulation device comprising:

housings forming an external shape of the magnetic field stimulation device and including a first housing and a second housing;

inner casings having an internal space and accommodated in an accommodation space provided in the housings, wherein a first casing and a second casing included in the inner casings form the internal space, the first casing has a shape corresponding to an inner surface of the first housing, and the first casing is coupled to the first housing so as to be in close contact with the inner surface of the first housing;

a magnetic field generating means disposed in the internal space and configured to generate a magnetic field;

a cooling medium stored in the internal space and configured to induce the cooling of the magnetic field generating means; and a first passageway and a second passageway connected to the internal space, wherein the cooling medium is liquid, and wherein the cooling medium enters or exits the internal space through the first passageway and the second passageway without leaking into the accommodation space provided in the housings.

2. The magnetic field stimulation device of claim 1, wherein the first casing comprises a first coupling portion protruding from an outer peripheral surface of the first casing along a periphery of the first casing and having a first fastening hole, and wherein the second casing comprises a second coupling portion protruding from an outer peripheral surface of the second casing along a periphery of the second casing and having a second fastening hole provided at a position corresponding to the first fastening hole.

3. The magnetic field stimulation device of claim 2, wherein the first housing and the second housing form the accommodation space, and wherein the first housing has a fastening groove provided at a position corresponding to the first fastening hole and the second fastening hole.

4. The magnetic field stimulation device of claim 3, wherein the first housing, the first casing, and the second casing are coupled to one another as the first fastening hole, the second fastening hole, and the fastening groove are fastened by a fastening means.

5. The magnetic field stimulation device of claim 3, further comprising:

an insert member fixedly coupled in the fastening groove and having an internal thread.

6. The magnetic field stimulation device of claim 3, wherein the second housing has a protruding portion provided on a junction surface of the second housing to which the first housing is joined, and the protruding portion extends and protrudes along the junction surface, and wherein the first housing has a coupling groove provided at a position corresponding to the protruding portion.

7. The magnetic field stimulation device of claim 6, wherein the first housing and the second housing are coupled to each other as the protruding portion and the coupling groove are fitted with each other.

8. The magnetic field stimulation device of claim 3, wherein the first casing has a first hole through which the cooling medium enters or exits the first casing, wherein the first housing has the first passageway through which the cooling medium enters or exits the first hole of the first casing, and wherein the second casing has the second passageway through which the cooling medium enters or exits the second casing.

9. The magnetic field stimulation device of claim 2, further comprising:

a first sealing member provided between the first casing and the second casing and configured to prevent the cooling medium from leaking into the accommodation space provided in the housings.

10. The magnetic field stimulation device of claim 9, further comprising:

a second sealing member provided between the first housing and the second housing and configured to prevent the cooling medium from leaking outside the housings.

11. The magnetic field stimulation device of claim 2, wherein the first casing comprises a seating portion having a shape corresponding to the magnetic field generating means so that the magnetic field generating means is seated on the seating portion.

* * * * *